United States Patent
Schultz

(10) Patent No.: US 8,820,157 B2
(45) Date of Patent: Sep. 2, 2014

(54) METHOD OF MEASUREMENT OF GLUTEN CONTENT IN A SAMPLE OF FLOUR

(71) Applicant: Irma Schultz, Buenos Aires (AR)

(72) Inventor: Irma Schultz, Buenos Aires (AR)

(73) Assignee: Irene Susana Bordas, Buenos Aires (AR)

( * ) Notice: Subject to any disclaimer, the term of this patent is extended or adjusted under 35 U.S.C. 154(b) by 42 days.

(21) Appl. No.: 13/743,859

(22) Filed: Jan. 17, 2013

(65) Prior Publication Data

US 2014/0196533 A1   Jul. 17, 2014

(51) Int. Cl.
*G01N 7/22*   (2006.01)
*G01N 33/10*   (2006.01)

(52) U.S. Cl.
CPC ...................................... *G01N 33/10* (2013.01)
USPC .......................................................... 73/169

(58) Field of Classification Search
CPC ....................................................... G01N 33/10
USPC .......................................................... 73/169
See application file for complete search history.

(56) References Cited

U.S. PATENT DOCUMENTS

| 3,169,395 A * | 2/1965 | Enoch et al. ..................... 73/169 |
| 4,953,401 A * | 9/1990 | Perten ............................. 73/169 |
| 6,250,147 B1 * | 6/2001 | Perten ............................. 73/169 |
| 6,428,993 B1 * | 8/2002 | Bech et al. ..................... 435/193 |
| 7,094,586 B2 * | 8/2006 | Bech et al. ..................... 435/193 |
| 2003/0059914 A1 * | 3/2003 | Bech et al. ..................... 435/193 |
| 2014/0065262 A1 * | 3/2014 | Giuliani et al. ................. 426/20 |

* cited by examiner

*Primary Examiner* — Andre Allen
(74) *Attorney, Agent, or Firm* — Defillo & Associates, Inc; Evelyn A. Defillo

(57) ABSTRACT

The present invention relates to a method for measuring the gluten content in a flour sample. The method includes preparing the flour, sifting it, and adding water, then pre-hydrating with water in a pre-hydrating mixer for a few seconds, until a sphere cohesive material (SCM) is obtained. Then, the sphere SCM is submerged in a container with salt water for a few minutes, to allow the structuring of the gluten. Then, the sphere is washed in a washing machine to eliminate the water soluble substances, which are not gluten. Then, the gluten structured with excess water is centrifuged in a "centrifuge", then removed from the centrifuge and weighed. The value that is read is the measurement of wet gluten. To obtain the value of the dry gluten, dry in a desiccation stove or a Teflon® dryer.

3 Claims, No Drawings

METHOD OF MEASUREMENT OF GLUTEN CONTENT IN A SAMPLE OF FLOUR

FIELD OF THE INVENTION

The present invention relates to a method of measuring gluten content in a flour sample. The method includes the preparation of a sphere of cohesive material (SCM) in a pre-hydrating mixer, then the sphere is submerged in a container with salt water for a few minutes, to allow the structuring of the gluten. The process continues by washing the sphere in a washing machine to eliminate the water soluble substances. Then, the structured gluten with excess of water is centrifuged in a centrifuge, removed from the centrifuge, and weighed. The reading value is the measurement of the wet gluten. To obtain the dry gluten content, the wet gluten is dried in a desiccation stove or in a Teflon® dryer.

One of the advantages of the present invention includes fully linking the gluten in structuring conditions, in flour samples with enough content of non-denatured gluten, which allows the use of many flour batches, which are currently discarded to be used for different types of industries.

PRIOR ART

The gluten includes various types of proteins, for example, the gliadin and glutenin. When these proteins come in contact with water, after mixing and kneading them, a homogeneous and strong formation is obtained, which is known as gluten.

The gluten is characterized as being a complex molecule that is insoluble in water. The gluten water absorption properties, as the viscoelasticity and thermocoagulation, differ from any other vegetable protein molecule.

The gluten provides a variety of industrial applications such as: baking, vegetables, meat, pasta, cold meats, dietetic products, balanced products, adhesives, and others.

The methods used to measure gluten in flour, previous to the present invention, were mainly of two types: manual method or mechanical method. Each one of these methods has difficulties in its measurement. For example, in the manual method, the measurement must be repeated until the same result is obtained, thus, to obtain a confirmation at least two measurements are required.

In the case of mechanical methods that are the most widely used today, these methods cannot be used to measure gluten values in flour samples that contain low amounts of gluten. These methods do not contemplate the structure of the molecules and in the washing step, thus, the little gluten content in the flour sample is loss, i.e. these methods are not compatible with the manual methods.

The method of the present invention is as fast as the mechanical method and measurements can be performed in flours that have small amounts of gluten, being also fully compatible with the manual method.

Also, the measurement carried out with the method of the present invention may be verified by performing an empirical confirmation, where it may be seen that it outperforms the methods that have been used until now. Until now, the gluten was measured within each system in a self-referential way; i.e. which was considered good measurement if the results were repeated, without considering the true amount of gluten.

To calibrate the method of the present invention, measurements were used with pattern samples of different known amounts of gluten. The calibrations were carried out to measure dry gluten and wet gluten. It was found that the method repeated the amount of dry gluten placed in advance and that wet gluten values were extrapolated, therefore the method of the present invention is reliable and accurate.

In addition, the obtained values were compared with the manual method giving equal results.

The difference between the mechanical method and the method of the present invention is mainly the novel steps, which are the hydration and cohesion of the molecules, i.e. the "structuring" of the gluten. These steps are not provided in the mechanical method, resulting in consequential erroneous measurements.

The structuring of the gluten comprises submerging the sphere that comes out of the mixer into a container with salt water for a few minutes. Then, the process continues with washing the sphere of structured material (SSM) with water inside a washing device.

The mechanical method washes the non-structured gluten, with the logical loss of gluten, in the washing process, therefore batches of flour are discarded, by not knowing the content of gluten; batches that can be used in different industries and different food preparations.

It should be clarified that the structuring of the gluten is the process of hydration and cohesion of the water insoluble gluten protein molecules, and the functional applications of gluten are unique and cannot be replaced by other products.

DESCRIPTION OF THE INVENTION

The measuring method of gluten contained in a flour sample includes the preparation of a sphere of cohesive material (SCM) from the flour sample obtained from the standardized known method, i.e. a pre-hydration is performed, 10 g of flour and 5 ml of water in a pre-hydrating mixer for 20 to 40 seconds to obtain a sphere of cohesive material (SCM). The sphere is immediately submerged in a container having salt water between 20 to 60 minutes or the sphere (SCM) is wrapped in a filter paper saturated with the salt water and it is allowed to stand from 40 to 80 minutes submerged in the container. Then, the sphere is washed in a washing machine to eliminate the water soluble substances (not the gluten). Then, the structured gluten with excess of water is placed in a centrifuge to remove the excess of liquid. It is removed from the centrifuge and is weighed on an analytical balance. The value found is the weight of wet gluten and through a math equation, the percentage of wet gluten in the sample is obtained. This is the measurement of the true wet gluten.

To obtain the dry gluten content, the true wet gluten is dried in a desiccation stove or a Teflon® dryer thermostat at 150° C. The dry gluten is weighed in a balance at 0.01 g and the calculations are carried out to obtain the percentage of dry gluten.

The properties of the gluten: water absorption, viscoelasticity and thermocoagulation make it different from any other vegetable protein and are why the measurement of gluten in flour may need to use a structuring method also special, which is the method of the present invention.

The gluten provides various industrial applications, as for example: baking industry, vegetables, meat industry, pastas, cold meats, sausages, and dietary products, balanced, or also in adhesives industry, and others.

One of the advantages of the present invention allows to quickly measure low gluten contained in flour, since the method comprises the full linking of gluten in structuring conditions with enough content of non-denatured gluten, making that many batches of flour, which are currently discarded, can now be used.

Example of Realization

Weigh 10.0 grams of flour or ground sample and transfer to the hydrator container with addition of 5 ml of a saline solution or add the necessary ml for the unification of the sphere of the material.

Activating the mixing machine for 20 sec. forming the SCM.

Submerging the SCM in a container with the saline solution for 30 minutes or wrapping the SCM in a filter paper soaked with saline solution for 50 minutes, until you obtain an SSM. This process is done to structure the gluten and prevent the gluten from being lost during the washing step. E.g. To earn time and perform the work in series, 5 to 10 containers may be processed with 1 SCM per container.

Place the SSM obtained in step 3 in the container of a washer and carry out the washing process until the washing water loses its turbidity and there are only trace amounts of starch.

Remove excess washing water: placing the SSM in the centrifuge. Centrifuge for 1 minute at 6000 RPM.

Calculations to Obtain the "Wet Gluten"

6.1 Weigh the wet gluten as it is in balance to 0.01 g.

6.2. Estimate the % of wet gluten, taking into account the mass of the wet gluten, the mass of the sample, and the percentage of moisture of the flour of the sample.

7.0 Obtain the "dry gluten": by drying for 5 minutes in a Teflon press thermostat at 150° C.

7.1 Weigh the dry gluten obtained in the balance to 0.01 g.

7.2. Calculate the dry gluten %, taking into account the mass of the dry gluten, the mass of the sample, and the percentage of moisture of the flour of the sample.

Calibration of the method, the objective of the calibration includes comparing the value of the measured magnitude (or represented) by the measuring system, with values that, under strictly defined conditions, produce known patterns or reference materials.

The calibration was carried out by comparing the manual method and the method of the present invention using several pattern samples with different known amounts of gluten, until the measurement of the dry gluten.

It was found that both the manual method and the method of the present invention repeated the amount of dry gluten released in advance, therefore are repeatable, reliable and substantially accurate.

This empirical verification transcends the methods that have been used until today, because until now, the gluten was measured within each system in a self-referential way; i.e. which was considered good measurement if the results were repeated, without considering that this is the true amount of gluten.

To confirm the quality of the test results of my invention, compared to other methods, tests were made with two groups of samples and three types of methods: the manual method, the method of the present invention, and the mechanical method.

The first group includes measuring of pattern samples valued previously with quantities of known dry gluten (M1; M2; M3; M4) and a second group that includes a group of unknown flour samples (Gr 1; Gr2; Gr.3) from samples of commercial grains of wheat bread.

In the group of pattern samples, the glutens were measured by the manual method and the method of the present invention.

The pattern samples are produced with the following composition:

| Composition shows pattern | | | | |
|---|---|---|---|---|
| Pattern sample | M1 | M2 | M3 | M4 |
| Gluten | 10.0 | 20.0 | 30.0 | 40.0 |
| Corn starch | 90.0 | 80.0 | 70.0 | 60.0 |
| TOTAL | 100 g | 100 g | 100 g | 100 g |

M1 gluten content 10%;
M2 gluten content 20%;
M3 gluten content 30%;
M4 gluten content 40%

The unknown flour samples were from commercial samples of wheat grain bread (Gr1; Gr2; Gr3).

Gr1

Gr2

Gr3

Standard equipment for the manual method and the mechanical method were used as indicated in the rules of measurement of gluten.

The pattern samples M1-M2-M3-M4 were analyzed by the manual method and the method of the present invention.

The unknown samples Gr1-Gr2-Gr3 were processed by the three methods: the manual method, the method of the present invention, and the mechanical method until getting to the wet gluten and the dry gluten procedure was continued by using a stove.

Then, the confirmation was made to verify whether the final quantities in the pattern samples match the initials of the essay.

| 1. | INSTRUMENTAL |
|---|---|
| 1.1 | Cyclonic mill for experimental grinding (includes sieves). |
| 1.2 | Balance, allowing you to appreciate the 0.01 g |
| 1.3. | 10 ml automatic pipette, graduated to 0.1 ml. |
| 1.4 | Chronometer (timer) |
| 1.5. | Mixer apparatus mixer/hydrator programmed for the preparation of sphere of cohesive material (SCM) |
| 1.6 | Device programmed to wash the spheres of structured material (SSM) |
| 1.7 | Wash water collector |
| 1.8 | Containers to hold the spheres of cohesive material (SCM) of flour. |
| 1.9 | Filter papers |
| 1.10 | Centrifuge of 6000 RPM programmed with an automatic shut-off timer |
| 1.11 | Press device for Teflon® drying thermostattized to 150° C. |
| 1.12 | Laboratory drying stove at 105° C. |

| 2. | REACTIVOS |
|---|---|
| 2.1. | Distilled water |
| 2.2. | Sodium chloride |
| 2.3 | 20% Sodium chloride solution (saline solution) |

Manual Method

Mill for grinding up flour, sifted; prepare 10 grams of the flour, add 4.9 ml of saline solution in a mortar or similar container, of appropriate size, mix, crush and stretch, let stand for 5 minutes, and wash to remove starch and soluble substances. Then, remove the excess water by hand or with using a centrifuge, weigh in a balance at 0.01 g, to obtain the true wet gluten, carry out the calculations to obtain the measurement of the wet gluten, dry in a drying stove, and weigh in a balance at 0.01 g, and carry out the calculations to obtain the dry gluten.

Mechanical Method

Mill for grinding grain to flour, sifted, prepare 10 grams of flour, add 4.9 ml of saline solution in washer mixer for 20 sec, wash up to eliminate starch 8 minutes, centrifuge for 1 minute at 6000 RPM, weigh in the balance at 0.01 g, to obtain the true wet gluten, carry out calculations to obtain the measurement of the wet gluten, dry for 5 minutes in a Teflon® desiccation press thermostattized to 150° C., weigh in the balance at 0.01 g, and carry out the calculations to obtain the dry gluten.

Method of the Present Invention

Grinding of the flour grain, sift, prepare 10 grams of flour and add 4.9 ml of saline solution in the mixer/pre-hydrating mixer for 20 seconds, submerge the sphere of the material in the saline solution for 30 minutes, wash up until eliminating the starch 8 minutes, centrifuge 1 min at 6000 RPM, weigh in the balance at 0.01 g to obtain the true wet gluten, carry out the calculations to obtain the measurement of wet gluten, dry 5 minutes in the Teflon® desiccation press thermostattized to 150° C., weigh in the balance at 0.01 g, and carry out the calculations to obtain the dry gluten.

The table shows the values from the measurements of gluten in the analysis of pattern samples (M1; M2; M3 and M4) and the unknown flour samples of wheat grain bread (Gr1; Gr2 and Gr3) subjected to the trials of obtaining the wet gluten and the subsequent verification as dry gluten, that were carried out by three different methods (manual, the present invention, and mechanical).

| Samples | M1 | M2 | M3 | M4 | GR1 | GR2 | GR3 |
|---|---|---|---|---|---|---|---|
| MANUAL method % wet gluten | 22.4 | 45.3 | 70.2 | 85.5 | 37.0 | 36.7 | 33.6 |
| Mechanical method % wet gluten | | | | | 31.8 | 22.6 | 27.3 |
| Method of invention % wet gluten | 22.1 | 45.5 | 70.0 | 85.5 | 37.2 | 36.4 | 34.0 |
| MANUAL method I % dry gluten | 9.8 | 19.7 | 29.8 | 40.0 | 14.8 | 14.3 | 13.2 |
| Mechanical method % dry gluten | | | | | 12.7 | 9.1 | 10.9 |
| Method invention % dry gluten | 10.0 | 19.8 | 30.1 | 39.8 | 14.8 | 14.5 | 13.3 |

Source: Own elaboration. January 2012.

The trials made with the mechanical method were made at the Camara Arbritral de la Bolsa de Cereales de Bs. As. The trials for the manual method and the method of the present invention were made at the Lab-Schultz-Bordas. C.A. de Bs. As . . . Argentina.

It is concluded that the method of the present invention has the advantage of repeating, to the end of the process, practically the amount of dry gluten present beforehand in the pattern sample, as well as in the manual method.

In view of this, the present inventor considers that both of the manual methods, as the method of the present invention, are correct in their measurements of gluten and they can be extrapolated with each other with other methods as if they were standard methods.

Trials with two variants of the SCM were made, submerged and wrapped in filter paper oversaturated with the saline solution, resulting in identically the same measurements.

From the trials with the unknown samples, results that the differential between the manual method and the method of the present invention, there are no differences, while among the method of the present invention and the mechanical method there are differences ranging between 14% and 36% in the measurement of dry gluten.

It follows that the method of the present invention should be applied at the receipt points of the merchandise due to its speed and accuracy for the analysis of the gluten amount present in the sample.

That it has been the invention and the way in which it has to be practiced, I declare in what rightly refers as my exclusive property, described as follows:

What is claimed is:

1. A method of measurement of a gluten content in a flour sample, the method comprising the steps of:
    1) weighing between 5 to 30 grams of a milled flour sample, passing the weighted flour sample to a hydrating mixer, adding between 3 and 8 ml of a saline solution;
    2) mixing during 14 to 30 seconds until forming a sphere of cohesive material SCM;
    3) submerging the sphere of step 2 into a container with the saline solution for 20 to 60 minutes or wrapping the sphere SCM in a filter paper wetted with the saline solution for 40 and 80 minutes;
    4) placing the sphere obtained in step 3 into a washer machine and washing the sphere until a wash water loses turbidity;
    5) placing the sphere obtained in step 4 in a centrifugal and centrifuge for 0.5 to 3 minutes at 6000 RPM; and
    (6) weighing the sphere of step 5 to obtain a wet gluten and calculating a percentage of wet gluten, drying the wet gluten for 2 to 15 minutes in a Teflon® press at 150° C. or at 105° C. in a laboratory drying oven, weighing the dry gluten and calculating a percentage of dry gluten.

2. A method of measurement of a gluten content in a flour sample, the method comprising the steps of:
    1) weighing 10 grams of a milled flour sample, passing the weighted flour sample to a hydrating mixer, and adding 5 ml of a saline solution;
    2) mixing during 20 seconds until forming a sphere of cohesive material SCM;
    3) submerging the sphere of step 2 into a container with the saline solution for 30 minutes;
    4) placing the sphere obtained in step 3 into a container of a washing machine and washing the sphere until a wash water loses turbidity;
    5) placing the sphere obtained in step 4 in a centrifugal and centrifuge for 1 minute at 6000 RPM; and
    (6) weighing a wet gluten and calculating a percentage of wet gluten, drying the wet gluten for 2 to 15 minutes in a Teflon press at 150° C., weighing the dry gluten and calculating a percentage of dry gluten.

3. A method of measurement of a gluten content in a flour sample, the method comprising the steps of:
    1) weighing between 10 grams of a milled flour sample, passing the weighted flour sample to a hydrating mixer, and adding 5 ml of a saline solution;
    2) mixing during 20 seconds until forming a sphere of cohesive material SCM;
    3) wrapping the SCM in a filter paper wetted with the saline solution for 50 minutes;
    4) placing the sphere obtained in step 3 into a container of a washing machine and washing the sphere until a wash water loses turbidity;
    5) placing the sphere obtained in step 4 in a centrifugal and centrifuge for 1 minute at 6000 RPM; and
    (6) weighing a wet gluten and calculating a percentage of wet gluten, drying the wet gluten for 5 minutes in a Teflon press at 150° C., weighing the dry gluten and calculating a percentage of dry gluten.

\* \* \* \* \*